United States Patent
Komann et al.

(10) Patent No.: US 11,472,602 B2
(45) Date of Patent: Oct. 18, 2022

(54) HOLDING STRUCTURE WITH A PLURALITY OF CONTAINERS HELD THEREON FOR SUBSTANCES FOR PHARMACEUTICAL, MEDICAL OR COSMETIC APPLICATIONS, AND TRANSPORT OR PACKAGING CONTAINER HAVING SAME

(71) Applicant: Schott Schweiz AG, St. Gallen (CH)

(72) Inventors: Christian Komann, Speicher (CH); Arne Kloke, St. Gallen (CH); Anil-Kumar Busimi, St. Gallen (CH)

(73) Assignee: SCHOTT Schweiz AG, St. Gallen (CH)

( * ) Notice: Subject to any disclaimer, the term of this patent is extended or adjusted under 35 U.S.C. 154(b) by 45 days.

(21) Appl. No.: 16/685,514

(22) Filed: Nov. 15, 2019

(65) Prior Publication Data
US 2020/0156824 A1    May 21, 2020

(30) Foreign Application Priority Data
Nov. 16, 2018    (DE) ...................... 20 2018 106 510.6

(51) Int. Cl.
*A61J 1/16* (2006.01)
*B65D 25/10* (2006.01)
(Continued)

(52) U.S. Cl.
CPC ............ *B65D 25/108* (2013.01); *A61J 1/062* (2013.01); *B65D 77/0446* (2013.01)

(58) Field of Classification Search
CPC .. B65D 25/108; B65D 77/0446; B65D 71/70; B65D 85/30; A61J 1/062; A61J 7/0069; A61J 1/16
(Continued)

(56) References Cited

U.S. PATENT DOCUMENTS 6,462,276 B2 * 10/2002 Shimizu ................... H02G 3/26
                                                          174/659
9,403,619 B2    8/2016 Deutschle et al.
(Continued)

FOREIGN PATENT DOCUMENTS

CN         103359348 A      10/2013
DE    20 2016 107 209 U1    5/2018
(Continued)

OTHER PUBLICATIONS

Extended European Search Report dated Mar. 19, 2020 for European Patent Application No. 19208739.3 (6 pages).

*Primary Examiner* — Steven A. Reynolds
(74) *Attorney, Agent, or Firm* — Taylor IP, P.C.

(57) ABSTRACT

A combination includes: a holding structure including receptacles which are arranged in a regular arrangement and are formed by peripherally formed side walls; containers received in the receptacles, the containers having a basic body which, at an upper end, merges into a shoulder portion which is adjoined by a narrowed neck portion with a widened upper edge with an opening; holding projections provided at lower ends of the receptacles and configured to hold the containers in the receptacles, the holding projections at the lower ends protruding radially inwards into the receptacles, the containers being supported directly on the holding projections; and centering elements provided above the holding projections and configured to center the containers in the receptacles. The centering elements have a beveled configuration and protruding into the receptacles in order to reduce a width of the receptacles at the lower ends thereof in a funnel shape.

22 Claims, 9 Drawing Sheets

(51) Int. Cl.
   *A61J 1/06*    (2006.01)
   *B65D 77/04*   (2006.01)

(58) Field of Classification Search
   USPC .................................... 206/438, 370, 478
   See application file for complete search history.

(56) References Cited

U.S. PATENT DOCUMENTS

| | | | | |
|---|---|---|---|---|
| 2010/0203643 | A1* | 8/2010 | Self .................. | B01L 9/06 |
| | | | | 436/47 |
| 2011/0226662 | A1* | 9/2011 | Nicoletti ............ | B65D 5/503 |
| | | | | 206/562 |
| 2012/0181285 | A1* | 7/2012 | Krauss ............... | A61J 1/16 |
| | | | | 220/507 |
| 2013/0048531 | A1* | 2/2013 | Nicoletti ............ | A61M 5/002 |
| | | | | 206/557 |
| 2015/0306259 | A1* | 10/2015 | Deutschle .......... | A61B 50/30 |
| | | | | 422/3 |
| 2017/0183113 | A1* | 6/2017 | Deutschle .......... | F26B 5/06 |
| 2018/0134423 | A1* | 5/2018 | Narvekar ........... | B65B 55/20 |
| 2018/0208377 | A1 | 7/2018 | Kloke et al. | |

FOREIGN PATENT DOCUMENTS

| | | |
|---|---|---|
| EP | 3 136 109 A1 | 3/2017 |
| EP | 3 381 828 A1 | 10/2018 |
| WO | 2017/038878 A1 | 3/2017 |

\* cited by examiner

HOLDING STRUCTURE WITH A PLURALITY OF CONTAINERS HELD THEREON FOR SUBSTANCES FOR PHARMACEUTICAL, MEDICAL OR COSMETIC APPLICATIONS, AND TRANSPORT OR PACKAGING CONTAINER HAVING SAME

CROSS REFERENCE TO RELATED APPLICATIONS

This application claims priority to German Application No. 20 2018 106 510.6 filed Nov. 16, 2018, the contents of which are incorporated herein by reference.

BACKGROUND OF THE INVENTION

1. Field of the Present Invention

The present invention relates generally to the treatment of containers for substances for pharmaceutical, medical or also cosmetic applications, and it relates in particular to a holding structure with a plurality of containers held thereon for substances for pharmaceutical, medical or also cosmetic applications, for example vials, ampoules or carpoules, or of more complex Assemblies Having Such Containers.

2. Background

Medicament containers, for example vials, ampoules or carpoules, are widely used as containers for the storage of medical, pharmaceutical or cosmetic preparations for administration in liquid form, in particular in pre-dosed quantities. These medicament containers generally have a cylindrical shape, can be produced from plastics or from glass and can be obtained in a cost-effective manner in large numbers. In this respect, the containers are increasingly being delivered in holding structures in a predetermined geometric arrangement to a pharmaceutical manufacturer or to a subsequent processing operation and are further processed while the containers are held or received in the holding structure. For this purpose, cost-effective and durable holding structures are required in which the containers are held or received in an arrangement which takes up the least possible space.

The holding structures usually have guide portions which promote the insertion of the containers into receptacles of the holding structure, and positioning portions for precise positioning of the containers. At the same time, the highest possible packing density is to be made possible.

CN 103359348-A discloses a holding structure in the form of a trough-shaped holding tray, having a bottom on which there are provided a plurality of vertical positioning pegs which at the same time serve as guide portions for inserting the containers into the receptacles formed by the positioning pegs. However, the containers are held with comparatively large play. The achievable packing density of the containers is relatively small.

WO 2017/038878 A1 discloses a further holding structure, having a plate-shaped carrier on which there are formed a plurality of cylindrical receptacles having peripherally formed side walls. The cylindrical receptacles are arranged at a comparatively small distance from one another.

German Utility Model DE 20 2016 107 209 discloses a further holding structure of the aforementioned type in which inner receptacles of the holding structure are formed by axially extending positioning cylinders and separating webs which connect the positioning cylinders to one another. Although this arrangement allows a higher packing density of the containers, the production of the holding structure by plastic injection molding is comparatively complicated.

For a wide variety of reasons, use is generally made, according to the prior art, of holding structures in which the receptacles are formed by peripheral side walls. For holding containers having a cylindrical basic body, the receptacles here always have either a circular basic shape or the basic shape of a quadrangle, namely a square or rectangle, or of a hexagon, which entails a certain play in the receptacles and makes positioning and centering difficult.

SUMMARY OF THE PRESENT INVENTION

Exemplary embodiments disclosed herein provide an improved holding structure for simultaneously holding a plurality of containers for substances for pharmaceutical, medical or cosmetic applications, which holding structure permits precise positioning and centering of the containers in the receptacles. According to further aspects of the present invention, a holding structure of this kind is to be able to be produced easily and cost-effectively and in particular is intended to permit an advantageously high degree of stiffness and a high packing density of the containers. Further aspects of the present invention relate to transport units or transport or packaging containers and to a sterile packaging structure having such a holding structure.

In some embodiments provided according to the present disclosure, a combination includes: a holding structure including a plurality of receptacles which are arranged in a regular arrangement and are formed by peripherally formed side walls; a plurality of containers for substances for pharmaceutical, medical or cosmetic applications received in the receptacles, the containers having a basic body which, at an upper end, merges into a shoulder portion which is adjoined by a narrowed neck portion with a widened upper edge with an opening; a plurality of holding projections provided at lower ends of the receptacles and configured to hold the containers in the receptacles, the holding projections at the lower ends protruding radially inwards into the receptacles, the containers being supported directly on the holding projections; and a plurality of centering elements provided above the holding projections and configured to center the containers in the receptacles, the centering elements having a beveled configuration and protruding into the receptacles in order to reduce a width of the receptacles at the lower ends thereof in a funnel shape.

BRIEF DESCRIPTION OF THE FIGURES

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF EMBODIMENTS

According to the present invention, a holding structure with a plurality of containers held thereon for substances for pharmaceutical, medical or cosmetic applications is provided. The containers have a basic body which, at an upper end, merges into a shoulder portion which is adjoined by a narrowed neck portion with a widened upper edge and an opening. The holding structure has a plurality of receptacles which are arranged in a regular arrangement and are formed by peripherally formed side walls. Here, the containers are received at least partially in the receptacles. Holding projections for holding the containers in the receptacles are provided at the lower ends of the receptacles. Holding projections at the lower ends protrude radially inwards into the receptacles.

According to the present invention, centering elements for centering the containers in the receptacles are provided above the holding projections at the lower ends of the receptacles. The centering elements have a beveled configuration and protrude into the receptacles in order to reduce a width of the receptacles at the lower ends thereof in a funnel shape.

In some embodiments, the containers are supported directly on the holding projections, without the basic body being clamped on the centering elements provided above these.

In this way, according to the present invention, self-centering of the containers can be achieved in a simple way. During the insertion perpendicularly from above, the containers can be guided with minimal friction to a desired position in the receptacles, without the danger of undesired jamming of the containers on the centering elements. The containers can thus also be removed again, reliably and with minimal friction, from the receptacles, for example for further processing of the containers in a lifted state, or in a state in which the containers have been removed completely from the receptacles in an upward direction.

The containers can, in principle, be received in an upright position in the receptacles and can bear with their closed bottoms, or edges at open ends, directly on the holding projections.

The containers can, in principle, also be received upside down in the receptacles, with their upper ends facing downwards to the lower ends of the receptacles. The shoulder portions can then be supported directly on the holding projections. According to some embodiments, upper ends of the containers can extend, with their widened edge portions provided there, through openings formed at the lower ends of the receptacles between the holding projections.

Figure 1A:
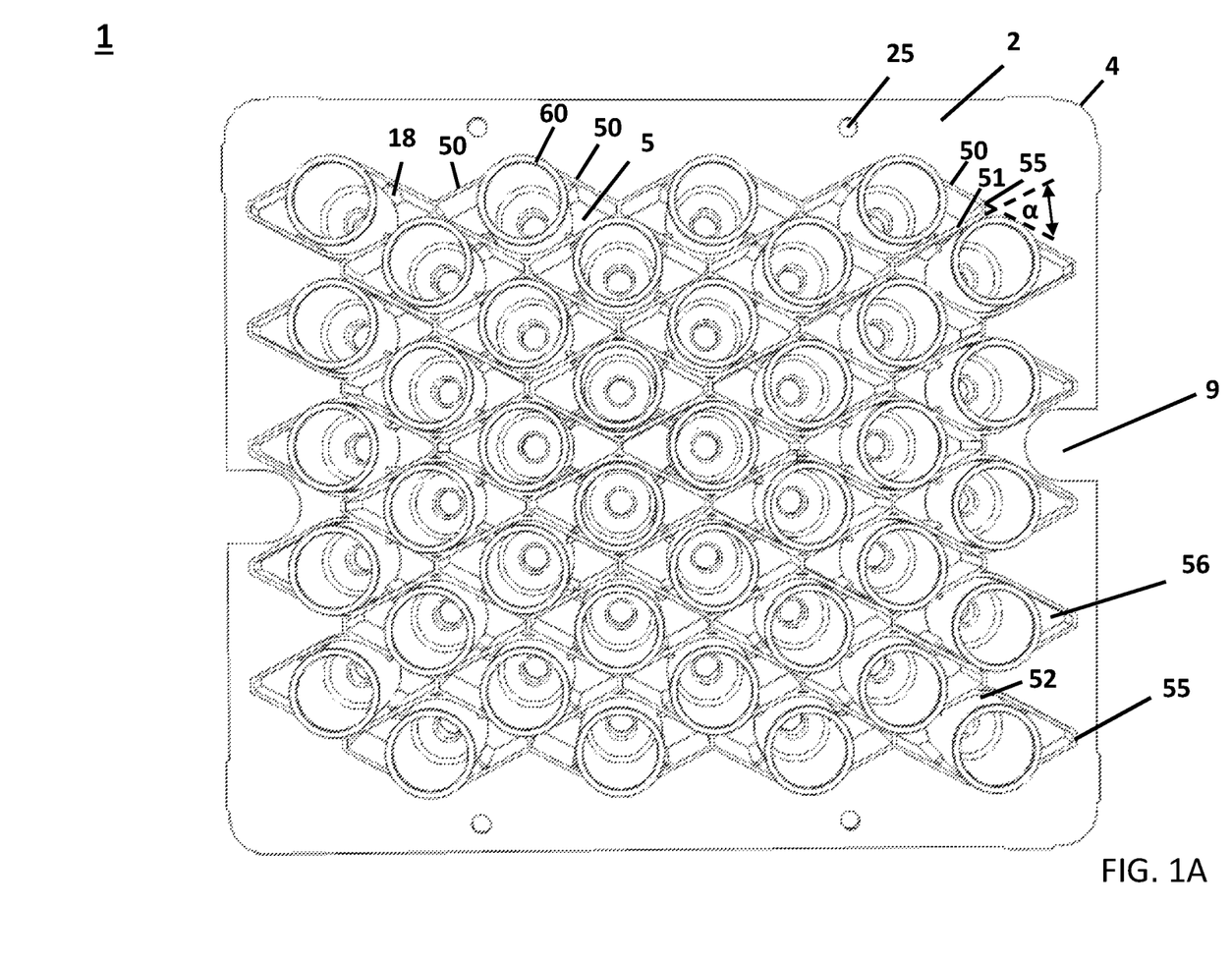
FIG. 1A is a schematic plan view showing a combination of a holding structure and a plurality of carpoules, which are held as intended on the holding structure.
Figure 1B:
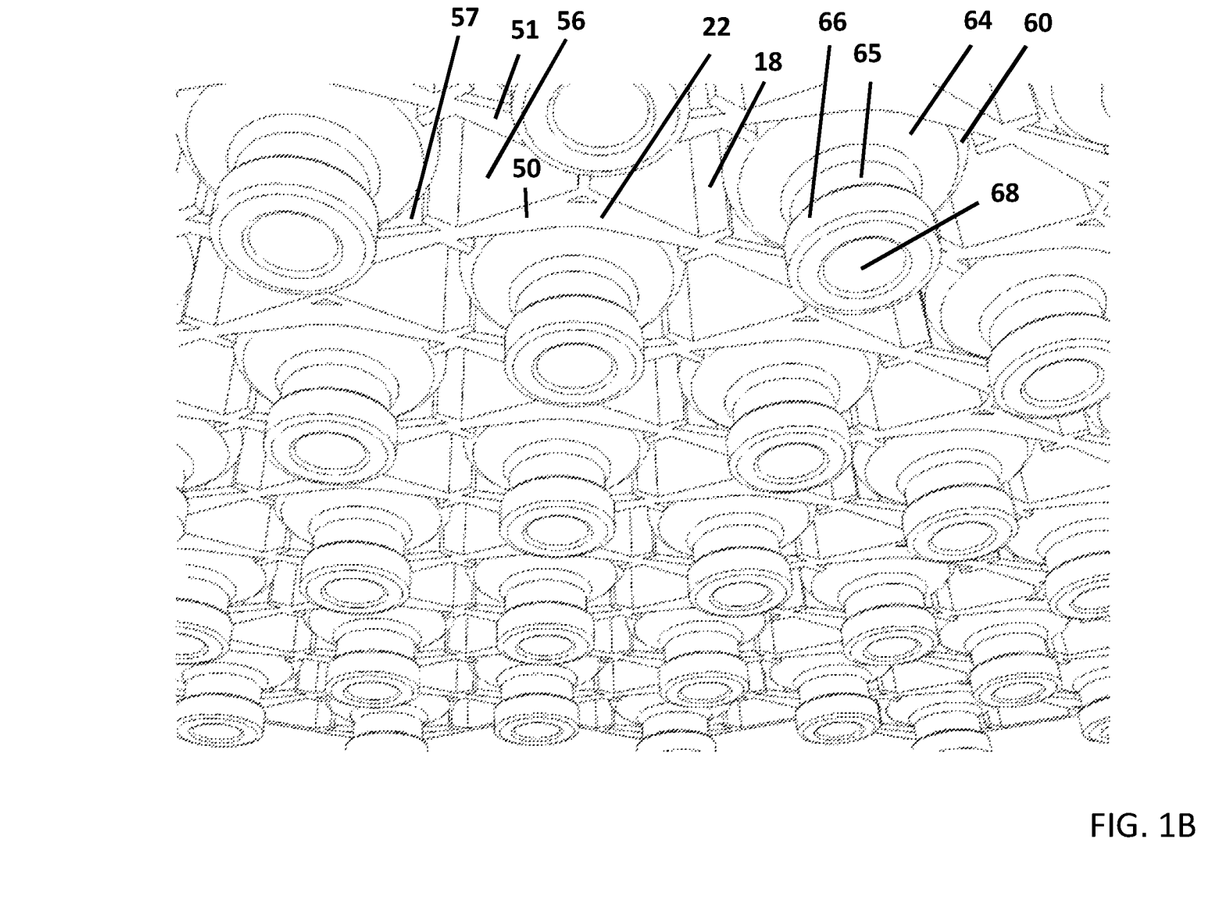
FIG. 1B shows the combination of FIG. 1A in an enlarged perspective partial view from below.
Figure 1C:
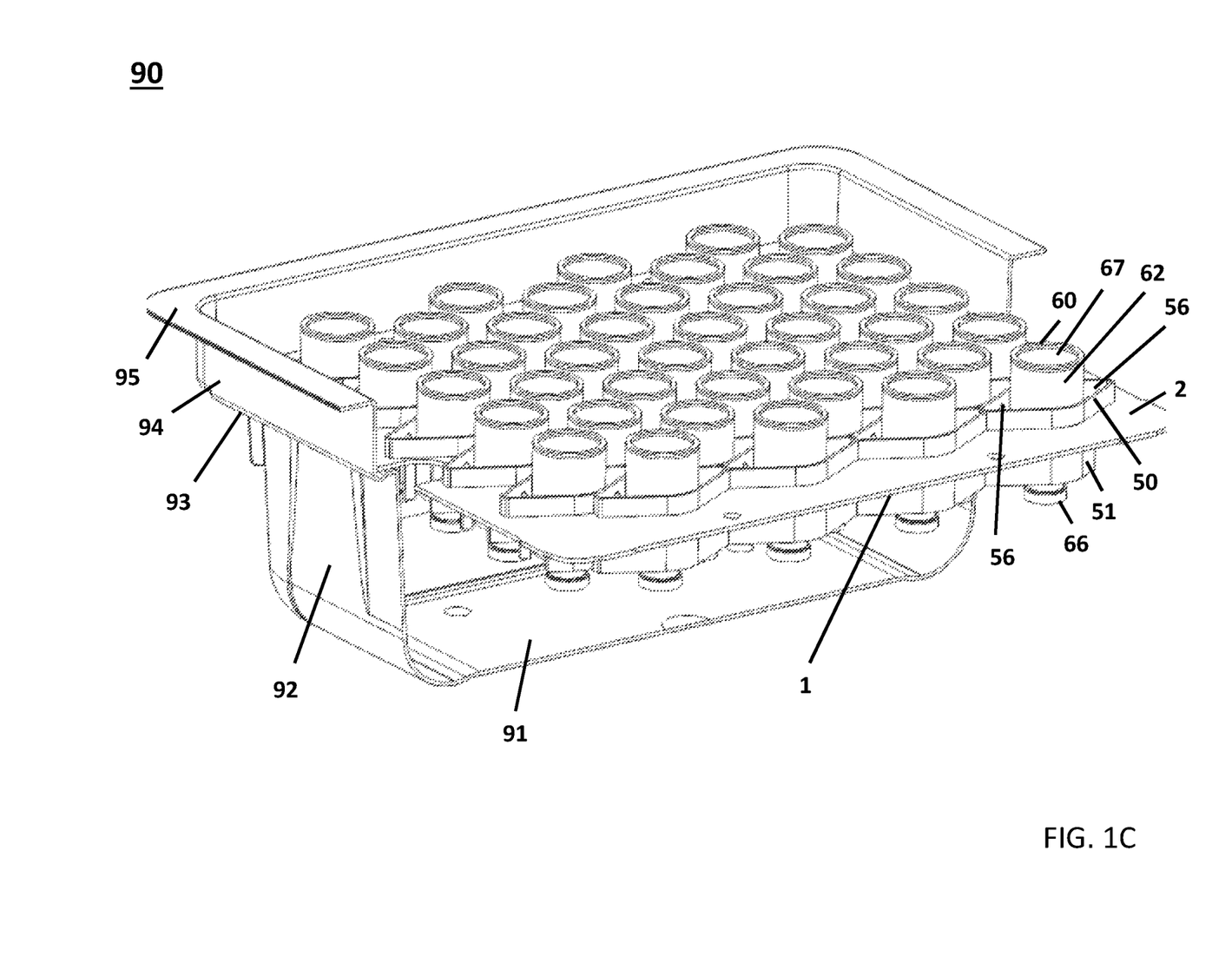
FIG. 1C is a schematic partial view showing the combination according to FIG. 1A received in a transport and packaging container.
Figure 1D:
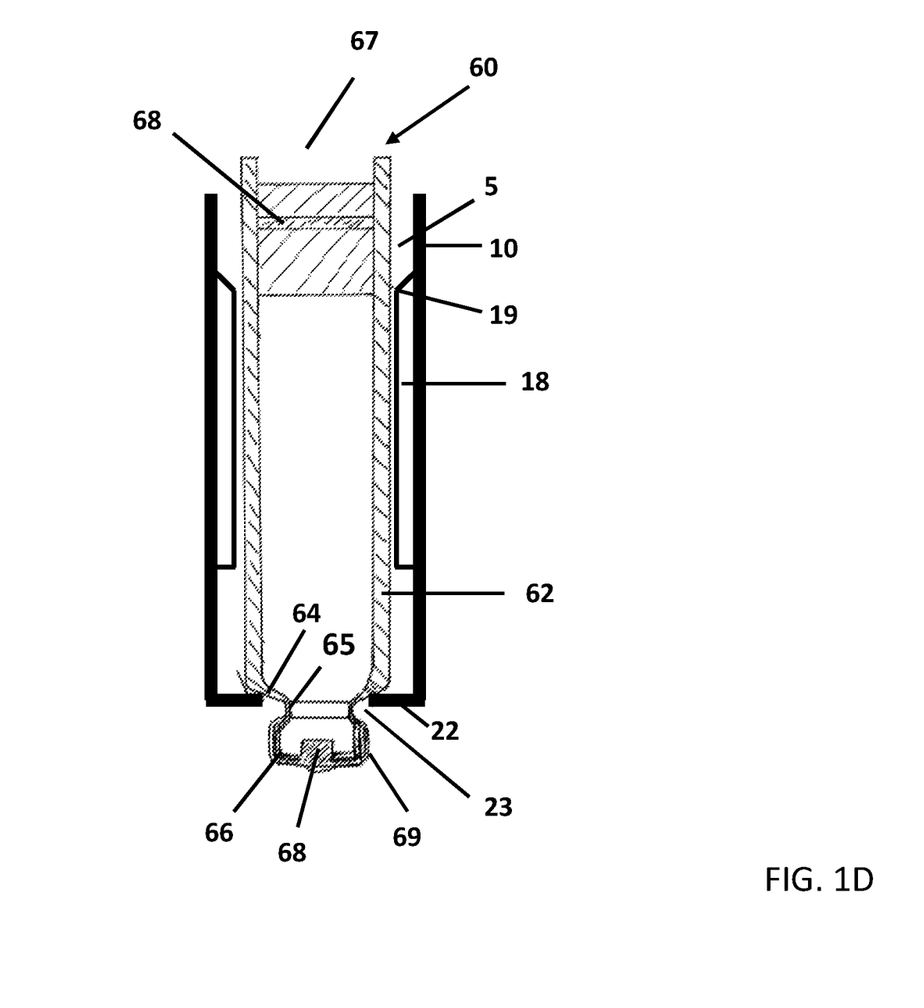
FIG. 1D shows a carpoule received in a receptacle of a holding structure provided according to a further embodiment.
Figure 1E:
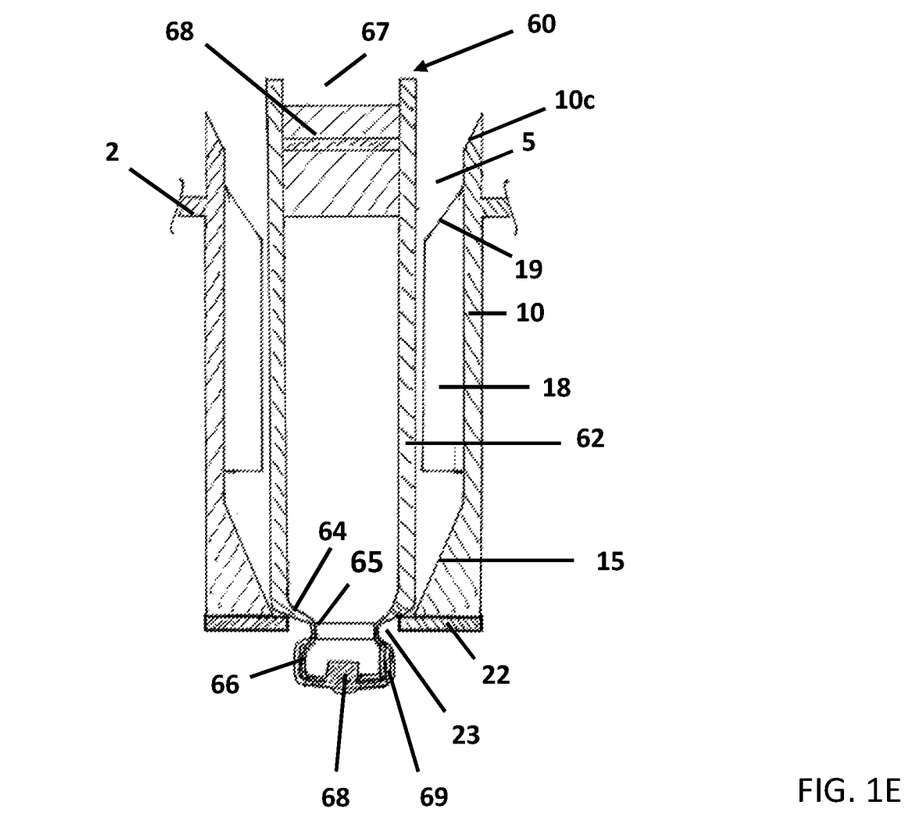
FIG. 1E shows a carpoule received in a receptacle of a holding structure according to FIG. 1A, with a modification at the lower end of the receptacle.
Figure 1F:
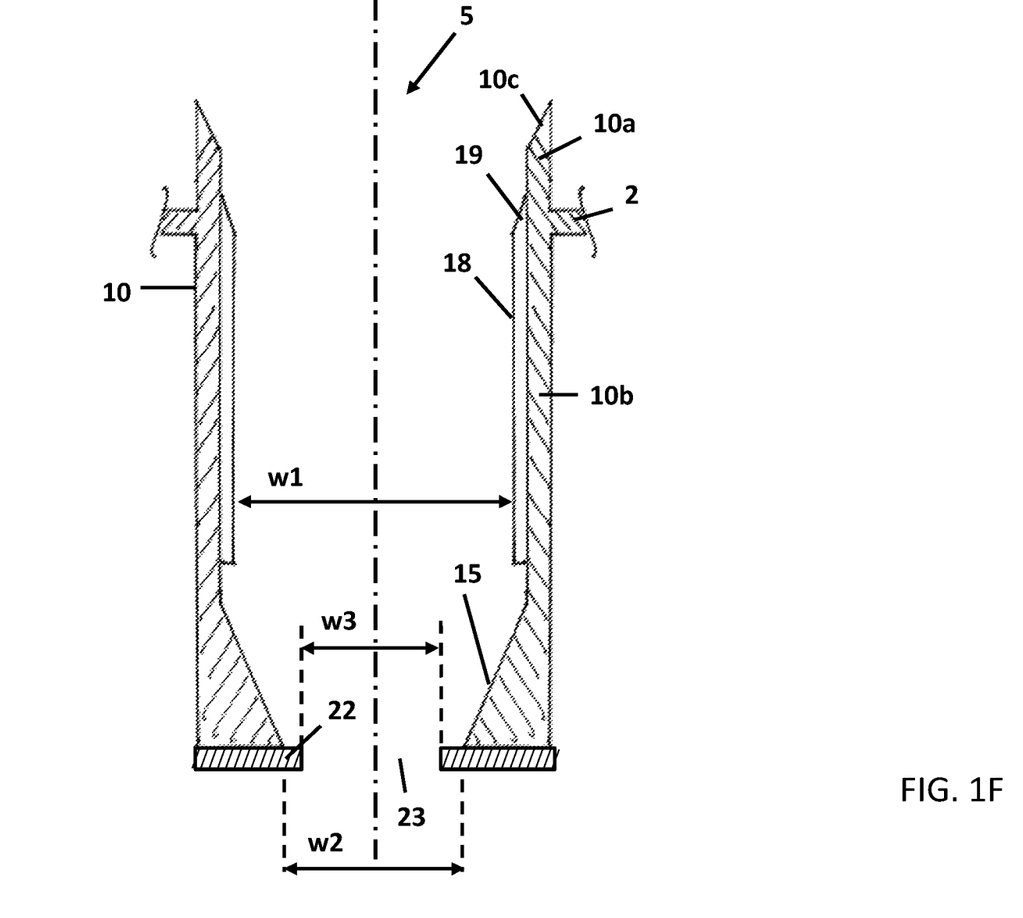
FIG. 1F is a schematic sectional view showing a receptacle of a holding structure provided according to the present invention.

The principle of self-centering of containers in the receptacles of a holding structure provided according to the present invention is described further herein with reference to FIG. 1F. The latter shows a schematic sectional view of a receptacle 5, which is formed by a peripheral side wall 10, with a portion 10a protruding from the upper side 2 of the holding structure 1, and with a portion 10b protruding from the lower side 2 of the holding structure 1. An annular, peripherally formed centering element 15 is provided at the lower end of the receptacle 5, which centering element 15 has a beveled configuration and protrudes into the receptacle 5 in order to reduce the width of the receptacle 5 in a funnel shape at the lower end to a width w2. The basic shape of the receptacle 5 is described in more detail further herein but, seen in plan view, can be circular, rectangular, for example diamond-shaped, and generally with n corners (with n≥4). The shape of the centering elements 15 matches this basic shape of the receptacles 5. In particular, the centering elements 15 may protrude in the same way from all side wall portions of the receptacle 5.

According to FIG. 1F, guide ribs 18 extending in the longitudinal direction of the receptacle 5 can be provided on the side wall 10, which guide ribs 18 are expediently distributed at identical angular spacings relative to each other along the circumference of the side wall 10, that is to say in particular in a point-symmetrical arrangement. The maximum width w1 of an interior formed by the guide ribs 18 is slightly greater than a maximum breadth or a maximum external diameter of the containers (not shown) that are to be received, such that the containers, during their insertion perpendicularly from above into the receptacles 5, slide without friction, or with minimal friction, into the receptacles 5 and in doing so are guided to a centered position.

According to the present invention, the centering elements 15 can be adjoined by holding projections 22. The centering elements 15 can define a minimum width w2 that is slightly greater than a maximum breadth or a maximum external diameter of the containers. The holding projections 22 at the lower ends of the receptacles 5 serve to directly support the containers in the receptacles 5. By virtue of the fact that the centering elements 15 have a beveled configuration, the containers, inserted perpendicularly from above into the receptacles 5, are automatically guided to a centered position. The risk of containers jamming on the centering elements 15 is avoided here, since the side walls 10 of the receptacles 5 have sufficient intrinsic stiffness and are not appreciably deformed, in particular not expanded, by the weight of the containers acting via the holding projections 22.

Between the holding projections 22, an opening 23 can be formed, as shown in FIG. 1F, of which the width w3 is smaller than the aforementioned minimum width w2 and smaller than the aforementioned maximum breadth or the maximum external diameter w1 of the containers. In this embodiment, the centering elements 15 serve exclusively to center the containers in the receptacles 5, whilst the containers, finally in a centered position in the receptacles, are supported on the holding projections 22.

Such an embodiment is suitable in particular for supporting containers that have a comparatively slim end, which can protrude downwards through the openings 23 of the receptacles 5 and which is adjoined by a gradually widening shoulder portion, as is described further herein by way of example with reference to FIGS. 1D and 1E. Examples of such pharmaceutical containers are in particular carpoules and vials, which can be received upside down in the receptacles 5 and can be supported at their shoulder portions directly on the holding projections 22, or syringe bodies, which can be supported on the holding projections 22 at their distal ends.

The supporting of a carpoule in the receptacles of a holding structure provided according to the present invention is described below with reference to FIG. 1C. Carpoules 60, like other pharmaceutical containers, customarily have a main body which is formed by a cylindrical side wall 62 which is adjoined by a tapering shoulder portion 64 and a narrowed neck portion 65, which in turn merges into a widened upper edge 66 having an ejection opening formed therein which is customarily closed by a plug 68 with a septum or the like which is axially secured on the upper edge 66 with a crimped-on metal cover 69. At an opposite end there is a filling opening 67 for filling and for subsequently receiving a plunger, of which a customary plunger stopper 70 is shown by way of example in FIG. 1E.

According to the present invention, the carpoules 60 are received upside down in the receptacles 5 of a holding structure. The shoulder portion 64 is supported directly on the two holding projections 22, without the basic body with the cylindrically formed side wall 62 being in any way clamped by the centering elements 15. In the optimally centered position, the cylindrical side wall 62 of a carpoule 60 does not touch the centering element 15 or the several centering elements 15 of a receptacle, such that jamming of the carpoule 60 is reliably prevented.

As is shown in FIG. 1E, the upper end with the widened upper edge 66 (and, where present, with the plug 68 fitted thereon and the metal cover 69) extends through the interspace 23 between the holding projections 22, such that the upper end is freely accessible from the lower side of the receptacles 5. In this state, the opposite ends of the carpoules 60 with the filling openings 67 project a little beyond the upper edge of the upper side walls 10 on the upper side of the carrier 2 out of the receptacles 5. During their insertion into the receptacles 5 perpendicularly from above, the carpoules 60 are guided and centered by the guide and positioning ribs 18.

According to FIG. 1B, a widened clearance 56 is formed on both sides of the carpoules 60 and allows access to the carpoules 60, which are received in the receptacles 5, for their handling (for example gripping, lifting or the like). Here, access can be had from the upper side and/or from the lower side of the carrier 2, as described below.

If an opening 23 is formed between the centering elements 15, as is shown in FIG. 1G, then the containers received in the receptacles can be supported with their shoulder portions directly on the holding projections 22. However, the opening 23 is not absolutely necessary.

In principle, the lower ends of the receptacles 5 can also have a closed configuration, in which case the holding projections 22 form a closed bottom. In such an embodiment, bottoms of containers, or edges at open ends of containers, can be supported directly on the holding projections 22, without the danger of the containers being clamped in any way by the centering elements.

In principle, the openings 23 at the lower ends of the receptacles 5 can also be formed with a very small diameter, for example in order to allow gas to flow into the interiors of containers received upside down in the receptacles 5, for example for the purpose of sterilization.

The centering elements 15 can be formed integrally with the holding projections 22. In principle, the holding projections 22 and centering elements 15 can also be formed separately, in particular also spaced apart from each other, as is shown schematically in FIG. 1F.

The inclined surfaces of the centering elements 15 can be designed to be resilient to a certain extent, in order to slightly clamp the carpoules 60 in the holding position, but they may also be non-resilient, such that the shoulder portion 64 is supported at a position whose internal diameter corresponds to the external diameter of the shoulder portion 64. Such bevels 15 can facilitate removal of the carpoules 60, in particular after forces acting downwardly from above the carrier 2 have acted on the carpoules 60, which is the case, for example, when placing plugs into the filling openings of the carpoules 60 and which, in the configuration according to FIG. 1D, on account of a certain spreading apart of the receptacles 5 at their lower ends, can lead to a certain degree of clamping between the holding projections 22 provided there.

As is shown in FIG. 1F, insertion bevels 19 can be formed at the upper ends of the guide ribs 18, in order to permit still better guiding of the containers during the gentle insertion of the latter perpendicularly from above into the receptacles 5. During the insertion of the containers perpendicularly from above into the receptacles 5, side wall portions or shoulder portions of the containers first come into contact with the beveled surfaces 10c of the guide ribs 18 and/or with the beveled surfaces of the centering elements 15 and are thus guided gently and with minimal friction to a precisely defined position in the receptacles 5, without any danger of undesired jamming of the containers.

Although FIGS. 1E and 1F show that there is a certain spacing between the guide ribs 18 and the beveled surfaces of the centering elements 15, it is also possible for the centering elements 15 to directly adjoin the guide ribs 18, in particular to be formed integrally with the latter.

The centering elements 15 and insertion bevels 10c can be formed peripherally and run toward one another in the manner of a funnel. However, a peripheral configuration of the beveled surfaces formed by the centering elements 15 and insertion bevels 10c is not absolutely necessary, since self-centering of the containers is, in principle, also possible without a peripheral configuration of the centering elements 15 and insertion bevels 10c.

According to some embodiments, the centering elements 15 and insertion bevels 10c can also have gaps, which may be desirable in particular if containers with a basic shape deviating from a circular shape are intended to be received in the receptacles 5. Examples of these are containers or more complexly designed units having a cylindrical basic body and one or more radially protruding extension pieces, for example so-called bypass carpoules (with laterally protruding bypass) or injection appliances. In such a case, the basic shape of the receptacles 5 may have a widened clearance or several widened clearances, as disclosed in detail further herein, in which a respective radially protruding extension piece is intended to be finally positioned upon insertion into the receptacles, i.e. with a desired angular orientation in the receptacles.

FIG. 1D shows the supporting of the shoulder portion 64 of a carpoule 60 directly on the holding projections 22 of a receptacle 5 of a holding structure 2 according to a further embodiment.

FIGS. 1A to 1C show examples of how the carpoules 60 are held on a holding structure 1 provided according to the present invention.

FIG. 1C further shows the arrangement of a combination of a holding structure 1 and a plurality of carpoules 60 held thereon in a transport and packaging container 90. According to FIG. 1C, the transport and packaging container 90 is substantially box-shaped or trough-shaped and has a bottom 91, a peripherally formed side wall 92 projecting perpendicularly therefrom, a step 93 projecting substantially at a right angle from said side wall, a peripherally formed upper side wall 94, and an upper edge 95 which is formed in the manner of a flange. The holding structure 1 bears directly on the step 93 of the transport and packaging container 90, such that the holding structure 1 is positioned precisely in the transport and packaging container 90 and the plurality of carpoules 60 are in this way arranged and held in a regular arrangement and at precisely defined positions. A protective film is applied to the upper edge 95 in a delivery state.

The basic shape of receptacles of a holding structure provided according to the present invention is described further herein in general terms with reference to FIGS. 1A to 1C.

The holding structure 1 has a plurality of receptacles 5 which are arranged in a regular arrangement (array) and serve for the reception of pharmaceutical containers, in particular of vials, carpoules or syringe bodies, or of more complexly designed assemblies having such pharmaceutical containers therein. The receptacles 5 have the basic shape of an n-gon, where n is greater than or equal to four. Exemplary shapes include a hexagonal basic shape (n=6), or a basic shape, as shown in the exemplary embodiment according to FIG. 1B, that is to say basically likewise a hexagonal basic shape, but which is distorted as explained in detail further herein.

In some embodiments, the containers 6 are at any rate received over the by far greatest part of their axial length in the receptacles 5 in order to prevent undesired tilting or wobbling of the containers in the receptacles during the transport of the holding structure 1. Here, the play of the containers 6 in the receptacles 5 is expediently set by guide ribs, as explained in more detail further herein.

The receptacles 5 are formed by side walls 50 which are formed peripherally, but this is not intended to exclude the possibility that, for example, for weight reduction or material saving, gaps or cutouts are formed at certain points in the side walls 50. The side walls 50 may project at right angles from the plate-shaped upper side of the holding structure 1. To facilitate demolding of the holding structure 1 from a mold used for injection molding, the side walls can, in principle, also be inclined in a radially inwardly directed manner at a comparatively small angle of, for example, at most 1° or at most 2° with respect to a perpendicular to the upper side 2.

By virtue of the polygonal basic shape of the receptacles 5, a common separating wall is formed between in each case two directly adjacent receptacles 5 and serves simultaneously as a side wall 50 of the two receptacles 5 adjacent to each other. This means that the side walls 50 are formed in one piece and from a solid material, that is to say rectangular in cross section. This should expressly not exclude the possibility that slots or cutouts are not after all provided on lower or upper ends of the side walls 50. At any rate, the side walls used in each case as a common separating wall are formed over at least 80% of their height from a solid material.

FIGS. 1A and 1B reveal the basic principle by which the receptacles 5 are designed, according to which the receptacles 5 are expanded at least in one direction perpendicular to the imaginary connecting line of two mutually directly opposite apexes, whereas the receptacles 5 are compressed in a direction perpendicular thereto, that is to say in the direction of this imaginary connecting line. In other words: the receptacles 5 are, as viewed in a plan view, starting from an imaginary point-symmetrical or mirror-symmetrical basic shape, compressed in a first direction, and expanded transverse to this first direction in a second direction, with the result that the gap in at least one region of the receptacles is widened to form a widened clearance 56 which facilitates handling of containers that are received in the receptacles 5.

In the illustrative embodiment according to FIG. 1A, the receptacles 5, in the plane of the drawing, are expanded both in a direction to the left and in a direction to the right. There are thus created two widened clearances 56 whose dimensions are considerably greater than the corresponding small clearances close to the two apexes. As is explained in more detail further herein with reference to FIGS. 2A to 2C, the widened clearances serve for access to the containers 6 received in the receptacles 5 by tools, for example grippers, tongs, lifting tools, plungers or the like, for handling and further treating the containers 6. As can be gathered from FIG. 1A, the dimensions of these widened clearances 56, in a direction perpendicular to the aforementioned imaginary connecting line, can indeed be of the order of magnitude of a diameter of the containers 6 received in the receptacles.

According to FIGS. 1B to 1C, the following advantages in particular can be achieved by the basic shape of the receptacles 5:

- free access from one side or from two opposite sides to a container received in a receptacle for handling by a handling tool, for example a gripper;
- by comparison to conventional holding structures, an achievable packing density that is higher by up to 20%;
- a higher degree of stiffness (upon exerting forces perpendicular to the holding structure, for instance when placing plugs into containers which are received in the receptacles of a holding structure, considerably less distortion of the holding structure occurs);
- more economical manufacture/shorter cycle times during the manufacture by injection molding/less outlay on material;
- lower mold complexity (lower investment costs, longer service life);
- during production by injection molding from a plastic, the mold requires few, large cores only on one side of the mold, which permits very good cooling of the mold and of a holding structure produced therein;
- containers or more complexly designed units whose basic shape differs from the circular basic shape can also be received in the receptacles: for example, so-called bypass carpoules (with laterally projecting bypass) can be received.

For a nest for holding cylindrical carpoules, it has been shown that, given the same base area of the carrier, the packing density can be increased by up to 58% (increase in the number of carpoules which can be held on a holding structure with a predetermined base area from forty carpoules to sixty-three carpoules with a simultaneous reduction in the weight of the nest from about 160 g to 113 g and for a comparable stiffness of the nest).

Figure 2A:
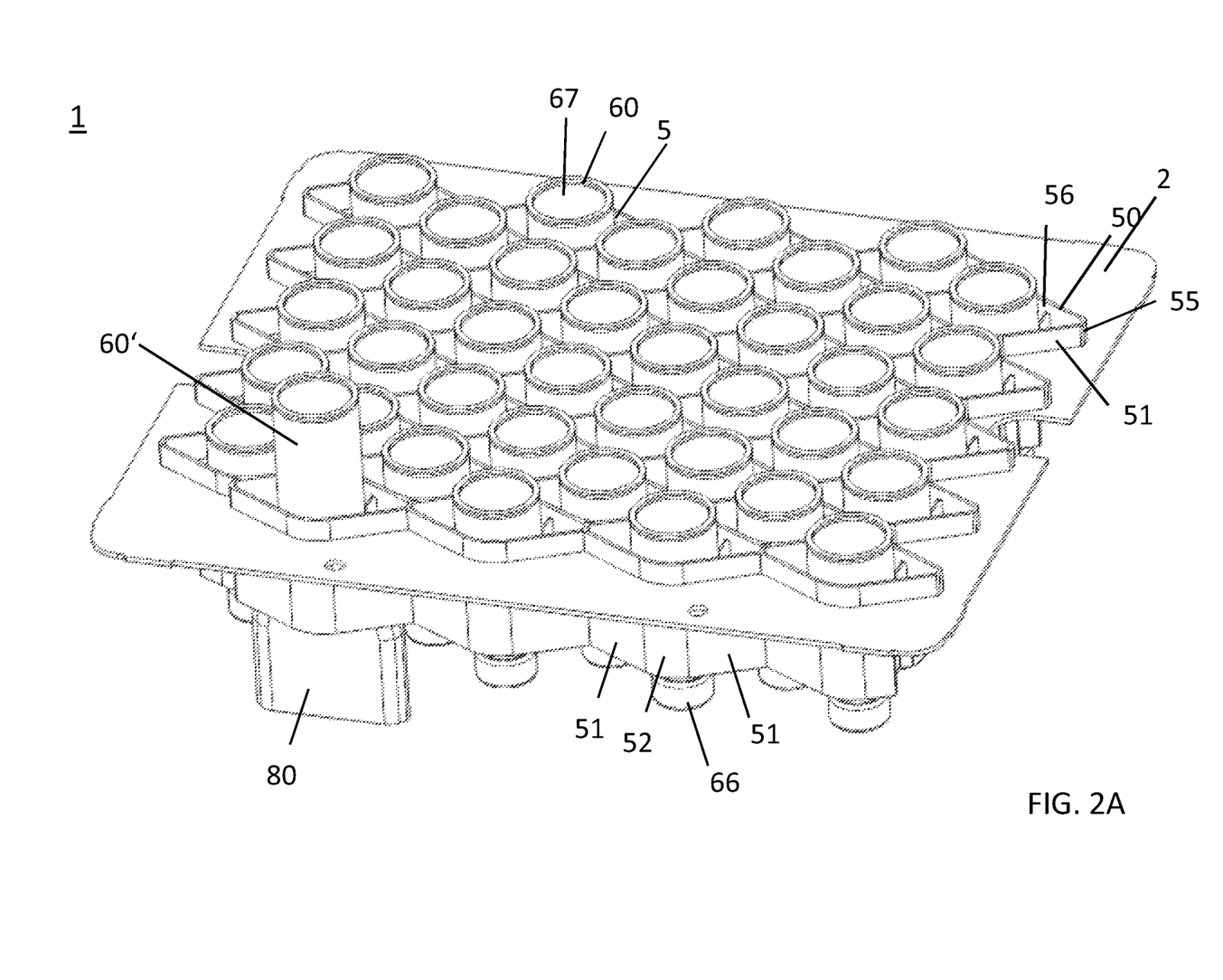
FIG. 2A is a perspective plan view showing a carpoule in a combination according to FIG. 1A being lifted by a tool which, according to the present invention, engages in the clearances of a receptacle assigned to the carpoule.
Figure 2B:
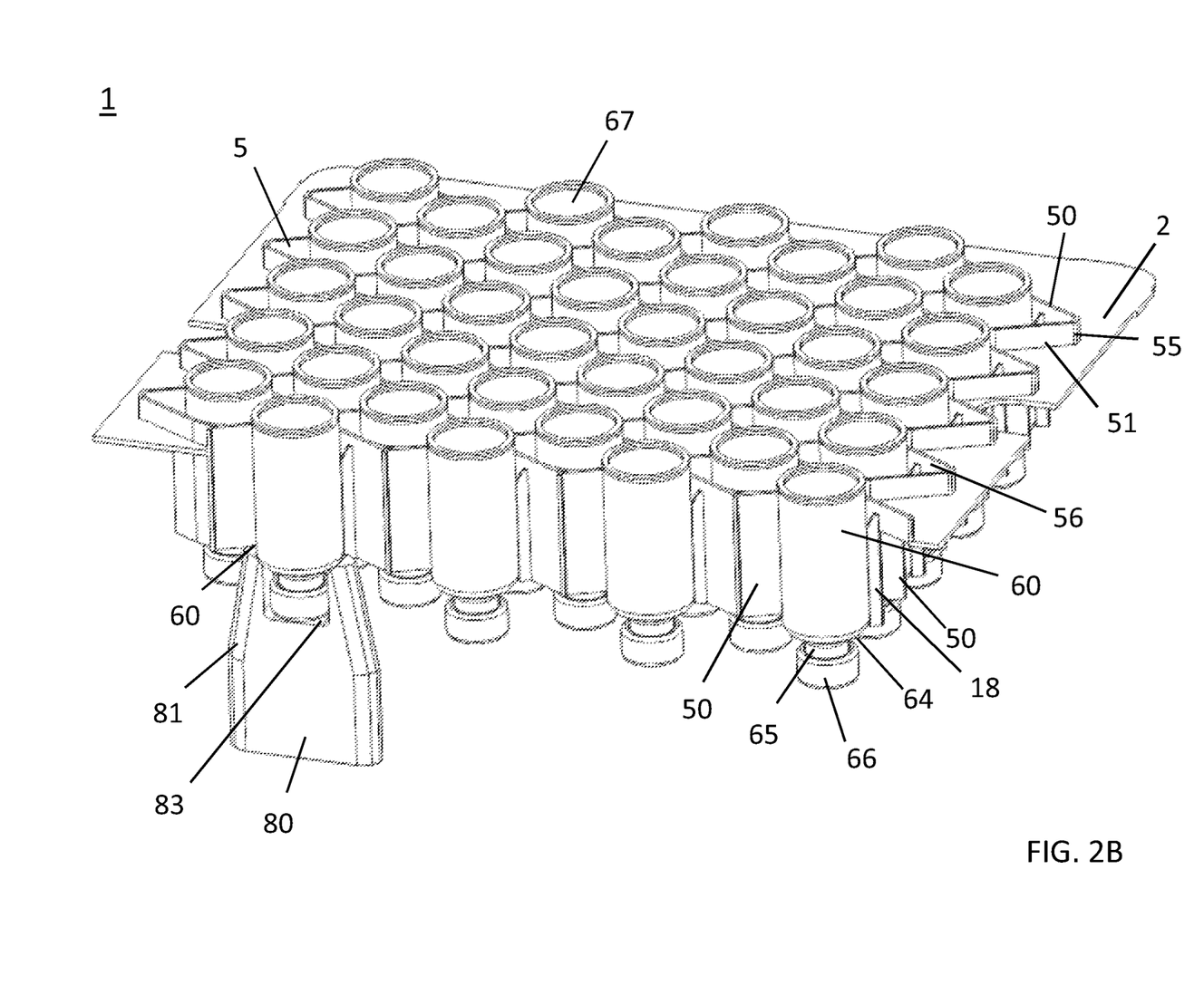
FIG. 2B is a perspective partial view showing the supporting of a carpoule in a combination according to FIG. 1A, before the carpoule is lifted.
Figure 2C:
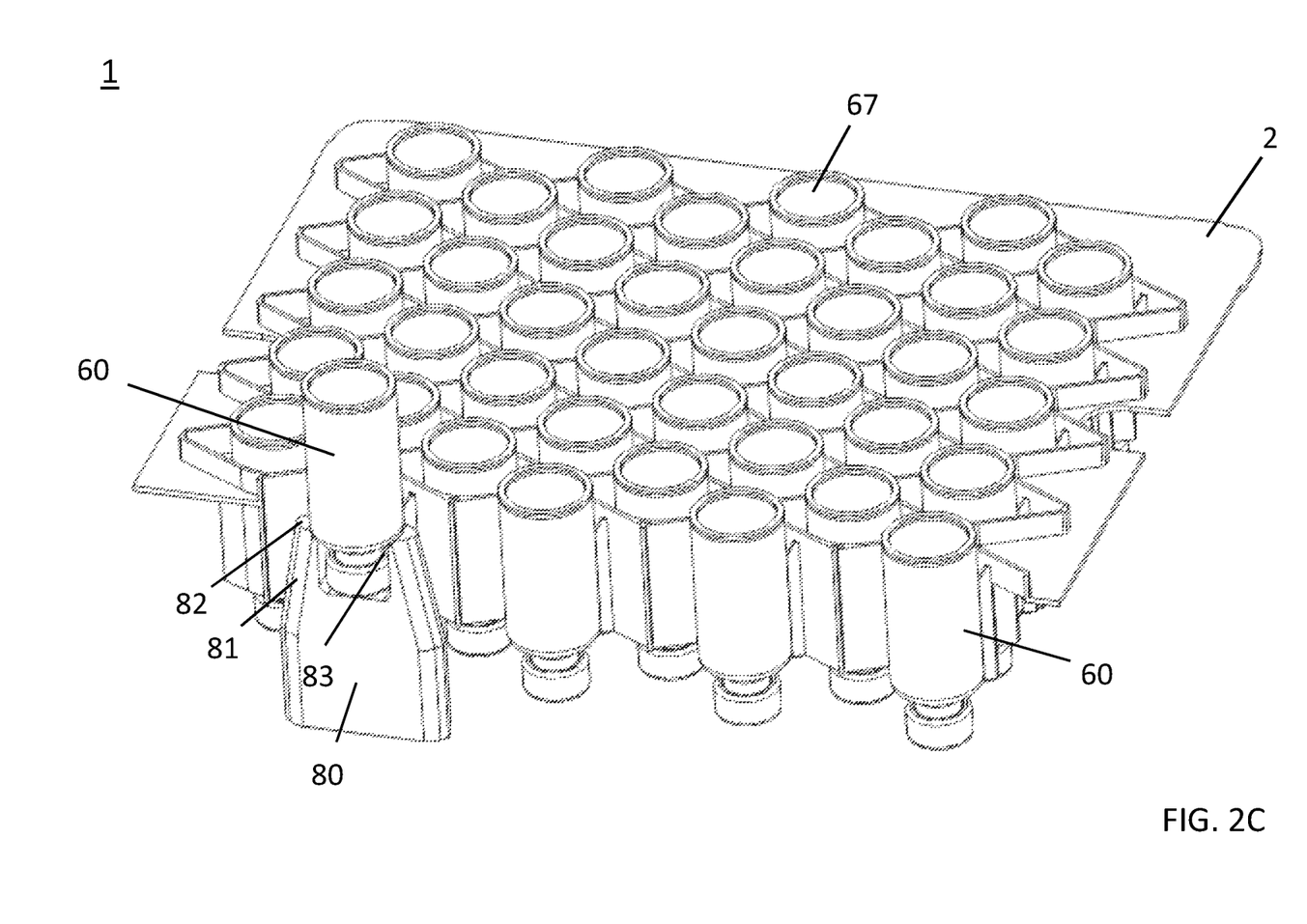
FIG. 2C is a perspective partial view showing the supporting of a carpoule in a combination according to FIG. 1A, in a lifted state of the carpoule.

The aforementioned widened clearances support handling of pharmaceutical containers that are received in the receptacles of a holding structure. With reference to FIGS. 2A to 2C, there is given below, as an example of such handling according to the present invention, the lifting of a carpoule 60 in a combination by a tool which according to the present invention engages in the widened clearances 56 of a receptacle 5, which is assigned to the carpoule 60, of the holding structure 1. According to FIGS. 2B and 2C, the tool 80 for handling has a rectangular basic body on whose upper end there are provided two handling arms 81 which converge towards one another at a small acute angle and, where appropriate, can be jointly pivoted about a common pivot point in the manner of tongs. Between the handling arms 81 there is formed a recess 83 into which there can project the widened upper edge 66 of the carpoule 60 with the metal cover possibly fastened thereon. The distance between the two handling arms 81 at their free upper ends 82 is chosen such that said distance substantially corresponds to the external diameter of the shoulder portion 64 of the carpoule 60. The breadth of the tool 80 is tailored to the dimensions of the receptacles 5, such that the tool 80 can be inserted to a sufficient extent into the receptacles 5 in order to lift the carpoules 60.

Upon insertion of the tool 80 from the lower side of the carrier 2 into the receptacles 5, the free upper ends 82 of the handling arms 81 finally come into contact with the shoulder portion 64 of a carpoule 60, as shown in FIG. 2B. During further lifting of the tool 80, the carpoule 60 is thus lifted into a lifted position 60', as shown in FIGS. 2A and 2C. In this lifted state 60', the carpoule 60 can be gripped by a gripping tool and transported away or be held for further treatment while the carpoule 60 is still partially received in the receptacles 5.

It is also possible in the same manner, by a modified tool, for whole rows or columns of carpoules 60 or for all carpoules 60 held on a holding structure 1 to be simultaneously handled, for example lifted or gripped. A tool designed in such a way can also be used for mechanically supporting the carpoules 60, for example if axially downwardly acting forces act on the carpoules 60, as is the case, for example, when placing plugs into the filling openings 67, in order thereby to counter bending of the carrier 2.

The handling arms 81 of the tool 80 can also be adjustable, for example to carry out a tongs like coordinated pivoting movement for gripping and releasing again a carpoule 60 received in a receptacle 5.

The intrinsic stiffness of the holding structure 1 particularly also allows further processing of the containers while they are received in the receptacles 5. It is conceivable for example that a holding structure 1 is placed along the edge of its lower side on a holding frame and then closure elements, for example closure plugs, are fitted onto the ends of the containers and the latter are displaced axially, such as at the same time for all the containers received in the holding structure or for one or more rows of containers. The forces prevailing here are compensated to a sufficient extent by the holding structure, with the result that only slight bending of the holding structure occurs (for example of at most 2.0 mm over the length of the holding structure), with the result that jamming of the closure elements can be avoided.

A holding structure 1, as described previously, can serve for storing and for transporting pharmaceutical containers, for example vials or carpoules. For handling, the holding structure 1 can be gripped and guided by gripping tools or the like by the access openings 9. The pharmaceutical containers can be further processed or treated while they are held by the holding structure 1, as described previously. For sterile transport, such a holding structure can be stored as a so-called nest in a trough-shaped transport or packaging container (so-called tub), for instance in the manner as described previously with reference to FIG. 1C. The transport or packaging container can be closed or sealed by a gas-permeable plastic film, in particular by a plastic film which is formed from a gas-permeable braid of plastic fibers and may be a TYVEK® film.

For sterile transport, such a transport or packaging container, where appropriate together with further transport or packaging containers of identical type, can be received in at least one sterile external packaging bag and be packaged in a sterile manner with respect to the environment. The at least one sterile external packaging bag can have a gas-permeable portion or even be formed completely thereby, which portion is formed in particular by a braid of plastic fibers, for example polypropylene fibers (PP).

As stated previously, the design of the holding structure is optimized in particular with respect to the achievable packing density. In the solution provided according to the present invention, the in each case adjacent walls of the receptacles are combined to form a wall used commonly by two adjacent receptacles. Thin-walled, easily breakable rib-like contours which are difficult to cool in the mold design can thus be avoided according to the present invention, resulting in a longer service life of the mold. Furthermore, the cycle time of the production process can be significantly shortened and piece costs can be reduced.

The conventionally round geometry of the receptacles is converted, according to the present invention, for relatively small volumes of the containers (for example up to 15 ml) into a hexagonal or diamond-shaped structure and for even greater volumes of the containers (for example of greater than 15 ml) into an octagonal structure in which a 45° and 90° arrangement of the receptacles is possible. Very high packing densities can thus be achieved. At the same time, the design of the mold for production by injection molding from a plastic is significantly simplified. Cooling of the molds and of the material can be realized in a very simple manner, and the cores of the molds can be produced in a simple and also standardized manner.

Furthermore, the design of the holding structure is also optimized with regard to stiffness and lightweight construction. In particular, the honeycomb design with side walls which are used commonly by adjacent receptacles and which are formed in one piece offers considerable advantages as regards the requirements placed on bending (bending of max. 2 mm with respect to the total area of the holding surface and measured in the empty state was able to be realized without problem).

The angular design of the receptacles in combination with the guide ribs simultaneously allows good accessibility for steam sterilization (for example, by ETO in an autoclave).

A horizontal (flat) mold parting additionally has a very advantageous effect on the parting forces during demolding of the holding structure and thus on the risk of the formation of disturbing flashes and thus potential particles as a result of mold wear. In addition, the mold parting no longer takes place in the direct region of the holding structure itself.

By virtue of the optimized position of the mold parting plane, a holding structure provided according to the present invention has proven in particular to be completely suitable for clean room conditions, because the risk of the creation of particles during demolding of the holding structure, but also during subsequent use, can be significantly reduced.

A holding structure within the sense of the present invention can be formed in one piece in particular by injection molding from a plastic. Also conceivable, in principle, is the production by 3D printing from a plastic. Thus, a further aspect of the present invention relates to a computer-readable or processor-readable file, also for transmission via networks, such as, for example, an in-house computer network or via the Internet, comprising instructions or control commands which, if these are downloaded by a computer or a processor, have the effect that a 3D printer under control by the computer or processor prints a holding structure, as disclosed in the present application, from a suitable material, such as a plastic material, in three-dimensional form.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE SIGNS

1 Holding structure
2 Plate-shaped carrier
4 Rounded-off corner region
5 Receptacle
6 Container
9 Access opening
10 Side wall
10c Bevel
15 Bevel
18 Guide and positioning rib
19 Insertion bevel of guide and positioning rib 18
20 Further guide and positioning rib
22 Holding projection
23 Opening
25 Opening
50 First side wall
51 Second side wall
55 Connecting web
56 Widened clearance for handling
57 Small clearance
60 Carpoule/Container
60' Carpoule in lifted position
62 Cylindrical side wall
63 Bottom
64 Shoulder portion
65 Narrowed neck portion
66 Upper edge
67 Filling opening
68 Plug
69 Flanged-on closure lid
70 Plunger stopper
80 Tool for handling
81 Handling arm
82 Front end of handling arm 81
83 Recess
α Convergence angle
w1 maximum width of receptacles 5
w2 minimum width of receptacles 5
w3 opening width of opening 23

What is claimed is:

1. A combination, comprising:
a holding structure comprising a plurality of receptacles which are arranged in a regular arrangement and are formed by peripherally formed side walls;
a plurality of containers for substances for pharmaceutical, medical or cosmetic applications received in the receptacles, the containers having a basic body which, at an upper end, merges into a shoulder portion which is adjoined by a narrowed neck portion with a widened upper edge with an opening;
a plurality of holding projections provided at lower ends of the receptacles and configured to hold the containers in the receptacles, the holding projections at the lower ends protruding radially inwards into the receptacles, the containers being supported directly on the holding projections; and
a plurality of centering elements provided above the holding projections and configured to center the containers in the receptacles, the centering elements having a beveled configuration and protruding into the receptacles in order to reduce a width of the receptacles in a funnel shape at the lower ends thereof, wherein a bottom edge of a beveled portion of the funnel shape ends directly at a respective holding projection.

2. The combination of claim 1, wherein a maximum width of the receptacles is slightly greater than a maximum breadth or a maximum external diameter of the containers and the centering elements define a minimum width which is slightly greater than the maximum breadth or the maximum external diameter of the containers.

3. The combination of claim 2, wherein the minimum width is at least 2% greater than the maximum breadth or the maximum external diameter of the containers.

4. The combination of claim 3, wherein the centering elements are formed integrally with the holding projections.

5. The combination of claim 1, further comprising guide ribs formed on the side walls that extend in a longitudinal direction of the receptacles, the guide ribs protruding inwards into the receptacles in a direction towards a geometric center of the respective receptacle.

6. The combination of claim 5, further comprising insertion bevels formed at upper ends of the guide ribs and inclined relative to the guide ribs.

7. The combination of claim 6, wherein the centering elements directly adjoin the guide ribs.

8. The combination of claim 1, further comprising an opening provided between the holding projections, a width of the opening is smaller than a width defined by the centering elements.

9. The combination of claim 8, wherein the containers are configured as carpoules or vials with a cylindrical basic body and are received upside down in the receptacles, wherein the shoulder portions of the carpoules or vials are supported directly on the holding projections such that the upper ends of the carpoules or vials extend through the openings and the cylindrical basic bodies are not clamped by the centering elements.

10. The combination of claim 1, wherein the containers are configured as vials with a cylindrical basic body and are supported on the holding projections without the cylindrical basic bodies being clamped by the centering elements.

11. The combination of claim 1, wherein an annular gap is formed between a cylindrical side wall of a container and a side wall of a respective receptacle, wherein, as viewed in a plan view, the receptacles, starting from an imaginary point-symmetrical or mirror-symmetrical basic shape, are compressed in a first direction and expanded in a second direction transverse to the first direction, with the result that the gap in at least one region of the receptacles is widened to form a widened clearance for handling containers which are received in the receptacles, and with the result that a width of the receptacles in the first direction is smaller than the width of the receptacles in the second direction transverse to the first direction.

12. The combination of claim 11, wherein the receptacles have a hexagonal basic shape or are derived from a hexagonal basic shape, wherein the width of the receptacles in the second direction is greater by at least 30% than the width of the receptacles in the first direction.

13. The combination of claim 12, wherein the widened clearance is formed by a corner region, which is formed by two side walls which, when viewed in plan view, converge towards a point or towards a short connecting web at a convergence angle α in order to form the widened clearance, wherein the following holds for the convergence angle: $0°<\alpha<110°$.

14. The combination of claim 11, wherein the centering elements are not formed peripherally and have at least one gap which is flush with a respective widened clearance of the receptacles.

15. The combination of claim 1, wherein the centering elements are formed peripherally.

16. The combination of claim 1, wherein a bevel is formed at an upper edge of the side walls, the bevel extends radially inwards and is formed peripherally, in order to make it easier to insert the containers from above into the receptacles.

17. The combination of claim 1, wherein a side wall is formed as a common separating wall between, in each case, two directly adjacent receptacles of the plurality of receptacles.

18. The combination of claim 17, wherein a height of the respective common separating wall substantially corresponds to an axial length of the two directly adjacent receptacles and the respective common separating wall is formed over at least 80% of the height from a solid material.

19. The combination of claim 17, wherein, when viewed in a cross section, the separating walls are, in each case, formed in one piece and without gaps.

20. The combination of claim 1, further comprising a plate-shaped carrier which forms an upper side of the holding structure, wherein the side walls and receptacles protrude perpendicularly from the plate-shaped carrier.

21. The combination of claim 1, further comprising a transport or packaging container having a box-shaped configuration, wherein the holding structure which has the plurality of containers held thereon is received in the box-shaped transport or packaging container in order to hold the plurality of containers in the transport or packaging container.

22. The combination of claim 21, wherein the transport or packaging container is received in at least one sterile external packaging bag and is packaged in a sterile manner with respect to the environment.

* * * * *